United States Patent [19]

Kowcz et al.

[11] Patent Number: 4,800,197

[45] Date of Patent: Jan. 24, 1989

[54] ANTI-ACNE COMPOSITION

[75] Inventors: Alexandra Kowcz, Monroe; Darrell G. Doughty, Derby, both of Conn.

[73] Assignee: Richardson-Vicks Inc., Wilton, Conn.

[21] Appl. No.: 74,821

[22] Filed: Jul. 17, 1987

[51] Int. Cl.$^4$ .................... A61K 31/60; A61K 31/615
[52] U.S. Cl. .................................... 514/162; 514/159; 514/859
[58] Field of Search ........................ 514/159, 162, 859

[56] References Cited

U.S. PATENT DOCUMENTS 4,318,907  3/1982  Kligman et al. .................... 514/164
4,608,370  6/1984  Aronsohn ............................. 514/159

*Primary Examiner*—Leonard Schenkman
*Attorney, Agent, or Firm*—David K. Dabbiere; Jack D. Schaeffer; Douglas C. Mohl

[57] ABSTRACT

A hydroalcoholic solution with pH 2-3.5 of salicylic acid and an anionic taurate surfactant selected from the group consisting of sodium methyl cocoyl taurate and sodium methyl oleoyl taurate.

7 Claims, No Drawings

ANTI-ACNE COMPOSITION

BACKGROUND OF THE INVENTION

This invention relates to improved cosmetically acceptable compositions for topical application to skin, particularly for the prevention or treatment of acne.

Acne is a follicular dermatosis. The comedo, which is the initial lesion of acne, resulting from the impaction of horny cells within the sebaceous follicle, develops in several stages. Primary comedones develop first as microcomedones where the follicular ostium begins to be distended by horny; material to form keratin plugs. The first visible lesion is the closed comedo or whitehead. Dilatation of the follicular ostium by dark pigmented horny material marks the onset of an open comedo or blackhead. Subsequent rupture of closed or open comedones results in formation of secondary comedones which are generally larger and more irregularly shaped.

The bricks of the horny framework of comedones are corneocytes (i.e., individual dead skin cells) which are held together by a cement-like substance of extracellular lipids. Closed and open comedones develop into the nodules and pustules identified with inflammatory acne. Although there are multiple factors that appear to be operative in the pathogenesis of acne, it is the formation of keratin plugs (i.e., It is therefore apparent that a treatment directed at preventing or dissolving such keratin plugs (keratolysis) would reduce the compaction necessary to produce the comedo as well as helping to unseat existing comedones (comedolysis).

Salicylic acid is a well recognized anti-acne active ingredient which causes a reduction in intercellular cohesion of the corneocytes (see C. Huber et al, Arch. Derm. Res. 257, 293-297, 1977), thereby dissolving the existing keratin plugs as well as preventing the formation of new ones. In order to best exert its keratolytic and comedolytic effect, the ideal anti-acne composition should deliver and retain optimal concentrations of salicylic acid in the stratum corneum with less penetration through the skin and into the general circulation.

According to the present invention, an effective antiacne composition is provided whereby substantial amounts of salcylic acid can be deposited into the stratum corneum with minimal penetration through the skin. The resultant increased efficacy of salicylic acid, as demonstrated by increased desquamation of corneocytes, occurs with less potential for irritation, drying of skin and systemic side effects.

DETAILED DESCRIPTION OF THE INVENTION

The anti-acne composition herein provided comprises a hydroalcoholic solution at pH 2 to 3.5 of salicylic acid as the active anti-acne ingredient together with a specific anionic surfactant component. More specifically, the subject invention provides a stable, hydroalcoholic composition having a pH value of from 2 to 3.5 and containing from about 0.2 to about 5.0 percent by weight of salicylic acid and from about 0.2 to about 5.0 percent by weight of sodium methyl cocoyl taurate and/or sodium methyl oleoyl taurate as the anionic surfactant component. Generally, a sufficient amount of a cosmetically acceptable alkaline component (i.e., alkalizing agent) to provide and maintain the composition with a pH from about 2.0 to about 3.5 is included. as the alcohol component of the hydroalcoholic solvent, from about 10 to about 60 percent by weight of ethyl alcohol, measured as total $C_2H_5OH$ content, is preferred although a like amount of isopropyl alcohol ($C_3H_7OH$) may also be beneficially utilized. From about 30 to about 80 percent by weight of water is also required as the aqueous component of the hydroalcoholic solvent.

As noted previously, salicylic acid is a well known active anti-acne ingredient. A listing of commercially available anti-acne products containing salicylic acid will be found in the Physician's Desk Reference for Nonprescription Drugs, 7th Edition, 1986, page 314.

The anionic surfactant component of the subject composition, i.e., the taurate surfactant component, is specifically directed to sodium methyl cocoyl taurate and sodium methyl oleoyl taurate, both of which are readily available from diverse commercial suppliers, as noted in The Cosmetic, Toiletry and Fragrance Association (CTFA) Cosmetic Ingredient Dictionary, 3rd Edition, 1982, pages 286–287.

The pH value of the subject compositions, from about 2 to about 3.5, may be achieved by use of appropriate cosmetically acceptable primary or dual buffer systems. In most instances, the resultant pH of the hydroalcoholic solution of salicylic acid is slightly below or at the lower end of the indicated range, and all that is required to adjust the pH to a desired higher value within the indicated range is to add an alkaline additive such as is commonly utilized in cosmetic formulations for such purpose. Although sodium carbonate is preferred, other suitable alkalizing agents include potassium carbonate, sodium hydroxide, potassium hydroxide, triethanolamine and the like. If deemed necessary to change or adjust the pH to a lower value, a suitable cosmetically acceptable acidifying agent such as citric acid may be employed.

The following table lists the general and preferred ranges of the essential components of the subject composition:

|  | % w/w | |
| --- | --- | --- |
|  | General | Preferrred |
| Salicylic acid | 0.2–5.0 | 0.5–2.5 |
| Taurate surfactant | 0.2–5.0 | 0.2–2.5 |
| Alcohol component | 10.0–60.0 | 20.0–50.0 |
| Water | 30.0–80.0 | 50.0–75.0 |
|  | pH 2–3.5. | |

It has been found that the compositions of this invention very effectively provide and maintain salicylic acid directly at the intended site of action, the stratum corneum, for optimal anti-acne effectiveness with minimal penetration through the skin into the general circulation. Such a surprising localization of action is deemed attributable to the selective use of the aforementioned taurate surfactant in the subject compositions. In contrast, as shown in the hereinafter Examples, other commonly utilized surfactants in the identical hydroalcoholic solution of salicylic acid (active ingredient) results in decreased localization in the stratum corneum and higher penetration of said active ingredient through the skin.

The following "Testing Protocol" is followed in obtaining the indicated data of the Examples.

Testing Protocol

A. Skin Penetration/Deposition

Excised human skin samples are obtained at autopsy and maintained under sterile conditions until used. The diffusion cell design and the methodology used in the skin penetration studies has been previously described by S. Nacht et al, J. Am. Acad. Dermatol. 4(1):31–37, 1981; also see "Percutaneous Absorption", Edited by R. L. Bronaugh & H. I. Maibach, Publ. by Marcel Dekker, Inc., N.Y., 1985, Chapter 29, "Artificial Membranes and Skin Permeability" by S. Nacht [& D. Yeung. The diffusion cell is composed of two compartments: the lower chamber is made of Plexiglass and the top is made of Teflon. The skin sample is mounted with the stratum corneum side exposed to the air and held on to the Teflon top with a rubber 0-ring; a tight seal between the two compartments is achieved by tightening the set screws. The cell has an effective diffusional area of 5.08 $cm^2$ and the dermis side of the skin is constantly bathed by filling the receptor compartment with 40 ml of isotonic saline. Adequate mixing of the receptor phase is accomplished with a magnet driven Teflon-coated stir bar moved by appropriate motor means located below the cell bath. The whole diffusion cell assembly is immersed in a water bath maintained at 30° C. using a circulating water bath. The test formulation (0.25 ml) containing radioactively labelled salicylic acid is added to the top of the epidermis. At hourly intervals over a period of seven hours, a one milliliter sample of the receptor fluid is withdrawn and analyzed for radioactive content by liquid scintillation counting means (Packard Tri-Carb model No. 460). Sample volumes are replaced with equal volumes of isotonic saline. All experiments are run in duplicate and the results averaged. Each set of experiments are performed with the skin from the same site from one donor.

At the end of the seven hour period the skin sample is removed from the diffusion cell, trimmed of excess skin and glued with cyanoacrylate glue to a glass plate. The surface of the skin is wiped with a methanol soaked swab to remove any product residue on the skin surface. Ten successive adhesive tape strippings are then taken and the salicylic acid content per strip determined. A more detailed discussion and description of tape strippings for measuring stratum conveum deposition is reported in "Skin Permeability" by "H. Schaefer et al, Publ. by Springer-Verlag, N.Y., 1982, pages 554-58.

B. Keratolytic/Desquamation Efficacy

It is reported in the literature that the efficacy of salicylic acid in various formulations to increase the desquamation rate of skin in vivo can be assessed by quantitating the number of corneocytes removed from the skin surface (see D. Roberts et al., Br. J. Dermatol., 103, 191–196, 1980; and M. C. Christensen et al, J. Invest. Dermatol., 71:289:294, 1978). Such quantification of removed corneocytes, as herein measured, utilizes one tape strip of the treated area after twice daily (6 hours apart) applications over a seven day period. The relative density of the corneocytes per tape strip is correlatable to the number of corneocytes removed. The density of the removed corneocytes is determined using a chromameter which measures the luminance value (L*) of reflected light off the tape strip when it is placed on a black background. The higher the L* value, the greater the number of corneocytes on the tape strip. Each formulation is applied to the inner forearm of human subjects at a dosage of 4 uL/$cm^2$ twice daily (6 hours apart) for seven days. Approximately 6 hours after the last application, the treated area is stripped once with adhesive tape. The experiment is performed with four subjects and the results averaged. The results are presented as a percent decrease in removed corneocytes as compared to untreated skin. A reduction in corneocytes is indicative of increased desquamation.

The subject compositions may also include optional additives such as, for example, antibacterial agents such as benzyl alcohol or methyl paraben; antioxidants and preservatives such as ethylenediamine tetraacetic acid; astringents such as witch hazel; odorants and sensates such as camphor or menthol; colorants and other cosmetically acceptable adjuvants generally utilized in topical anti-acne compositions. Although it is preferred to use the taurate surfactant as the sole surfactant in the subject compositions, other surfactants may be included, the nonionic type having preference over the anionic type in view of the relative non-irritating characteristic to the skin of the former. Cationic type surfactants, which are most irritating to the skin, are furthermore unsuitable because of their marked susceptibility to hydrolysis at the low acidic pH of the subject compositions. Obviously, the choice and amount of any additional ingredient should be such that said ingredient does not deleteriously counterbalance the beneficial characteristics herein ascribed to the taurate surfactant.

In accordance with the present invention, therefore, an improved cosmetically acceptable hydroalcoholic composition having a pH of about 2 to about 3.5 and containing an effective anti-acne amount of salicylic acid (0.2–5.0% w/w) together with an anionic surfactant is provided wherein the improvement comprises the use of sodium methyl cocoyl taurate or sodium methyl oleoyl taurate as said anionic surfactant (0.2–5.0% w/w).

| Ingredients | % w/w |
| --- | --- |
| Salicylic Acid | 0.05–2.00 |
| Na Methyl Cocoyl Taurate or Na Methyl Oleoyl Taurate | 0.7–2.0 |
| $C_2H_5OH$ (95% Ethanol) | 20–50 |
| Witch Hazel Distillate | 5–10 |
| Quaternium-22 | 0.6–1 |
| Aloe Vera Gel | 0.5–5 |
| Allantoin | 0–5 |
| $Na_2CO_3$ anhydrous | 0.01–0.8 |
| Citric Acid, hydrous | 3.5–4.5 |
| Menthol | 0.05–2 |
| Camphor | 0.00005–0.001 |
| Flavoring & Sensate Oils | 0.15–5 |
| Water, q.s. to 100%. | |

The following examples are intended to illustrate, but not to limit thereto, the present invention.

EXAMPLE 1

| | | % w/w |
| --- | --- | --- |
| Basic Formula: | $C_2H_5OH$ | 20.0 |
| | Salicylic acid | 0.5 |
| | Surfactant | 1.0 |
| | Sodium carbonate, to pH 3 | |
| | Water, to 100% | |

Respective hydroalcoholic solutions of salicylic acid are prepared respectively by substituting the following anionic surfactants, identified by their CTFA adopted names, in the Basic Formula:
(A)=Sodium methyl cocoyl taurate
B=Sodium dodecylbenzyl sulfonate
C=Sodium $C_{12-15}$ alcohols sulfate

EXAMPLE 2

The respective compositions of Example 1 are tested in vitro in accordance with Testing Protocol A and the resultant data demonstrate the enhanced localization of salicylic acid surfactants B and C, surfactant A provides a marked increase in the deposition of salicylic acid in the stratum corneum, measured in micrograms (ug), together with a marked decrease in the rate of penetration through the stratum corneum, measured in $ug/cm^2/hr$. The tabulated data for deposition represent the average of two sets of ten successive tape strippings and for the penetration rate, the average of two diffusion cells.

| Basic Formula With Surfactant | Salicylic Acid | |
|---|---|---|
| | Deposited (ug) | Penetration Rate ($ug/cm^2/hr$) |
| A | 412 | 0.8 |
| B | 318 | 4.6 |
| C | 270 | 3.3 |

EXAMPLE 3

In this example, the Basic Formula of Example 1 is modified by the indicated percentage of sodium methyl cocoyl taurate (surfactant A) and the resultant compositions are tested as in Example 2.

| w/w % of Surfactant A in Basic Formula | Salicylic Acid | |
|---|---|---|
| | Deposited (ug) | Penetration Rate ($ug/cm^2/hr$) |
| 0.25 | 232 | 7.5 |
| 0.75 | 267 | 6.9 |
| 1.25 | 236 | 8.0 |
| 2.50 | 178 | 11.3 |

EXAMPLE 4

This example demonstrates the decrease in efficacy afforded by another anionic surfactant, sodium lauryl sulfate (surfactant D). It also demonstrates the relative efficacy p (surfactant A) and sodium methyl oleoyl taurate (surfactant E). The Basic Formula of Example 1 is similarly modified and tested in accordance with Testing Protocol A.

| % w/w of Surfactant A in Basic Formula | Salicylic Acid | |
|---|---|---|
| | Deposited (ug) | Penetration Rate ($ug/cm^2/hr$) |
| 0.75% A | 403 | 4.9 |
| 3.0% D | 282 | 11.0 |
| 2.0% E | 487 | 5.0 |
| 0.7% E | 423 | 3.3 |

The tabulated results demonstrate the similarity in activity between surfactants A and E, the two taurate surfactants of this invention. In contrast, the use of surfactant D, a commonly utilized anionic surfactant in cosmetic preparations, results in a marked decrease in deposition of salicylic acid in the stratum corneum and a marked increase in the penetration rate through the skin.

EXAMPLE 5

In this example, sodium methyl cocoyl taurate (surfactant A) is compared with the anionic surfactant, sodum lauryl sulfate (surfactant D), and the nonionic surfactant, polysorbate 20 (surfactant F), at an equivalent concentration in accordance with the prior examples. The results again indicate the marked superiority of the taurate surfactant.

| % w/w of Surfactant in Basic Formula | Salicylic Acid | |
|---|---|---|
| | Deposited (ug) | Penetration Rate ($ug/cm^2/hr$) |
| 1.0% A | 102.0 | 7.6 |
| 1.0% D | 69.8 | 22.2 |
| 1.0% F | 86.5 | 14.7 |

EXAMPLE 6

The three hydroalcoholic solutions of salicylic acid with surfactants A, B and C respectively, of Example 1 are tested in vivo in accordance with Testing Protocol B. The tabulated data for percent reduction in corneocytes again indicate the marked superiority of Surfactant A.

| Basic Formula With Surfactant | % Reduction in Corneocytes |
|---|---|
| A | 50.7 |
| B | 34.2 |
| C | 9.9 |

EXAMPLE 7

This example illustrate preferred compositions of this invention containing additional optional ingredients. Each igredient is identified by its generic chemical name or by its CTFA adopted name.

| | % w/w | | |
|---|---|---|---|
| Ingredients | A | B | C |
| 1. Salicylic Acid | 2.00 | 0.50 | 1.00 |
| 2. Na Methyl Cocoyl Taurate | 0.72 | 2.00 | — |
| 3. Na Methyl Oleoyl Taurate | — | — | 0.70 |
| 4. $C_2H_5OH$ (95% Ethanol) | 35.00 | 20.00 | 50.00 |
| 5. Witch Hazel Distillate | 5.00 | 10.00 | 5.00 |
| 6. Quaternium-22 | 0.60 | 1.00 | 0.60 |
| 7. Aloe Vera Gel | 0.50 | 5.00 | 0.50 |
| 8. Allantoin | — | 0.10 | 5.00 |
| 9. $Na_2CO_3$ anhydrous | 0.1–0.2 | 0.01–0.05 | 0.15–0.8 |

-continued

| Ingredients | % w/w | | |
|---|---|---|---|
| | A | B | C |
| 10. Citric Acid, hydrous | 3.5–4.5 | 3.5–4.5 | 3.5–4.5 |
| 11. Menthol | 0.05–1.0 | 0.05–1.0 | 2.00 |
| 12. Camphor | 0.00005–0.001 | 0.00005–0.001 | 0.00005–0.001 |
| 13. Flavoring & Sensate Oils | 0.15–0.3 | 0.15–0.3 | 5.00 |
| 14. Water, q.s. to 100% | | | |

To a suitably sized vessel, add ingredients 4 and 5 with stirring at moderate speed. Add ingredients 1, 11 and 12 making sure each ingredient is completely in solution before the next addition. In a separate vessel, heat the taurate surfactant (ingredient 2 or 3) to 35°–40° C. until clear and then add ingredient 13 with stirring until homogeneous. Add the taurate mixture to the alcoholic salicylic acid mixture with stirring. Slowly add ingredient 14 and then add ingredients 6 and 7 and, in compositions B and C, add ingredient 8. Check pH and adjust to pH about 3 by adding ingredient 9 (to raise pH) and 10 (to lower pH) with stirring.

We claim:

1. A cosmetically acceptable composition for treating acne comprising:,
   (a) from about 0.2 to about 5.0 weight percent of salicylic acid;
   (b) from about 10 to about 60 weight percent of $C_2H_5OH$ or $C_3H_7OH$;
   (c) from about 30 to about 80 weight percent of water; and
   (d) from about 0.2 to about 5.0 weight percent of sodium methyl cocoyl taurate or sodium methyl oleoyl taurate; the composition having a pH value of from about 2 to about 3.5.

2. The composition of claim 1 wherein b) is $C_2H_5OH$ and (d) is sodium methyl cocoyl taurate.

3. The composition of claim 1 wherein b) is $C_2H_5OH$ and (d) issodium methyl oleoyl taurate.

4. A cosmetically acceptable composition for treating acne comprising
   (a) from about 0.5 to about 2.5 weight percent of salicylic acid;
   (b) from about 20 to about 50 weight percent of $C_2H_5OH$ or $C_3H_7OH$;
   (c) from about 50 to about 75 weight percent of water; and
   (d) from about 0.2 to about 2.5 weight percent of sodium methyl cocoyl taurate or sodium methyl oleoyl taurate; the composition having a pH value of from about 2 to about 3.5

5. The composition of claim 4 wherein b) is $C_2H_5OH$ and d) is about 0.7% by weight of sodium methyl cocoyl taurate.

6. The composition of claim 4 wherein b) is $C_2H_5OH$ and d) is about 0.7% by weight of sodium methyl oleoyl taurate.

7. A cosmetically acceptable composition for treating acne comprising:

| Ingredients | % w/w |
|---|---|
| Salicylic Acid | 0.50–2.00 |
| Na Methyl Cocoyl Taurate or Na Methyl Oleoyl Taurate | 0.7–2.0 |
| $C_2H_5OH$ (95% Ethanol) | 20–50 |
| Witch Hazel Distillate | 5–10 |
| Quaternium-22 | 0.6–1 |
| Aloe Vera Gel | 0.5–5 |
| Allantoin | 0–5 |
| $Na_2CO_3$ anhydrous | 0.01–0.8 |
| Citric Acid, hydrous | 3.5–4.5 |
| Menthol | 0.05–2 |
| Camphor | 0.00005–0.001 |
| Flavoring & Sensate Oils | 0.15–5 |
| Water, q.s. to 100% | |

* * * * *